(12) United States Patent
Jonchiere

(10) Patent No.: US 8,394,363 B2
(45) Date of Patent: Mar. 12, 2013

(54) COSMETIC RINSABLE MASK TYPE COMPOSITION FOR SKIN CARE

(75) Inventor: Claire Jonchiere, Ingre (FR)

(73) Assignee: LVMH Recherche, Saint Jean de Braye (FR)

( * ) Notice: Subject to any disclaimer, the term of this patent is extended or adjusted under 35 U.S.C. 154(b) by 267 days.

(21) Appl. No.: 12/281,736

(22) PCT Filed: Apr. 13, 2007

(86) PCT No.: PCT/FR2007/051114
§ 371 (c)(1),
(2), (4) Date: Dec. 31, 2008

(87) PCT Pub. No.: WO2007/122343
PCT Pub. Date: Nov. 1, 2007

(65) Prior Publication Data
US 2009/0130040 A1    May 21, 2009

(30) Foreign Application Priority Data
Apr. 14, 2006    (FR) ...................................... 06 03421

(51) Int. Cl.
*A61K 8/18*    (2006.01)
*A61K 8/73*    (2006.01)
(52) U.S. Cl. ................... 424/78.03; 424/401; 424/78.08
(58) Field of Classification Search ........................ None
See application file for complete search history.

(56) References Cited

U.S. PATENT DOCUMENTS

| | | | |
|---|---|---|---|
| 4,600,458 A | | 7/1986 | Kramer et al. |
| 5,626,154 A | * | 5/1997 | Rogers et al. ................. 132/200 |
| 6,139,829 A | * | 10/2000 | Estrin ........................ 424/78.08 |
| 2007/0077221 A1 | * | 4/2007 | Seigneurin et al. ........ 424/70.16 |

FOREIGN PATENT DOCUMENTS

| | | |
|---|---|---|
| FR | 2805461 | 8/2001 |
| WO | WO2004/009042 A | 1/2004 |
| WO | WO 2006/024768 | 3/2006 |

OTHER PUBLICATIONS

XP002451044; Emerging Technologies Inc.: "Norsocryl S-15, Technical Data" [Online], Jul. 7, 2007; URL:http://www.creativechemistry.com/uploads/norsocryl%20s-352.pdf.

* cited by examiner

*Primary Examiner* — Robert A Wax
*Assistant Examiner* — Sarah Park
(74) *Attorney, Agent, or Firm* — Woodcock Washburn LLP

(57) ABSTRACT

The invention relates to a cosmetic composition of rinse-off mask type for the care of the skin, characterized in that it comprises at least one superabsorbent polymer or copolymer of water-retaining type, in the form of particles in the substantially completely hydrated state, said particles having, in the dry or nonhydrated state, a mean particle size of between 5 and 100 μm, advantageously between 20 and 50 μm, in particular between 20 and 30 μm.

25 Claims, No Drawings

COSMETIC RINSABLE MASK TYPE COMPOSITION FOR SKIN CARE

The present invention relates to a cosmetic composition of rinse-off mask type for the care of the skin, in particular of the face or body.

The present invention relates more particularly to a cosmetic composition of rinse-off mask type for the care of the skin, in particular of the face or body, especially for removing skin pigment spots, such as age or sun spots, for improving the moisturizing of the skin, for obtaining a calming, soothing or relaxing effect, for stimulating skin microcirculation, for the purpose of improving the radiance of the complexion, in particular of the face, for obtaining a seboregulating effect for the care of greasy skin, or also for obtaining a slimming effect on certain parts of the body.

A composition of mask type is generally provided in the form of a gel or cream. It is generally intended for the care or hygiene of the skin or also to provide a sense of well-being. It is intended to be applied to the skin of the face but also to other parts of the body. Unlike a patch, a composition of mask type does not in itself usually comprise any solid support, such as occlusive or nonocclusive film, of woven or nonwoven textile type or of porous or nonporous plastic type.

According to a notion well known to a person skilled in the art, the term "composition of rinse-off mask type" is understood to mean a cosmetic composition formulated in order to be applied to the skin in a relatively thick layer and left for a certain period of time, generally from a few minutes to several tens of minutes, and in order to be, at the end of this period of time, peeled off, rinsed off with water or also simply wiped off.

In the context of the invention, the term "composition of rinse-off mask type" is understood to mean a composition formulated in order to be applied to the skin in a relatively thick layer and left for a certain period of time, generally from a few minutes to several tens of minutes, and in order to be, at the end of this period of time, rinsed off with water, in order to break it down and remove it, or also to be simply wiped off.

STATE OF THE ART

The document FR-A-2 805 461 discloses skin scrubbing agents and novel cosmetic compositions with a skin scrubbing or exfoliating effect comprising at least one crosslinked polymer or copolymer capable of absorbing water known as "superabsorbent agent". In order to obtain a skin scrubbing or exfoliating effect, the particles of crosslinked polymers or copolymers used must have a satisfactory particle size, indicated as being more than 100 µm, in particular between 100 and 800 µm, in the context of the commercial product (Flocare™).

In the field of masks, there is known a bleaching mask which uses an agent with a bleaching cosmetic effect.

For example, the document EP-0 362 450 discloses a cosmetic composition in the form of a mask with a regulating activity on skin pigmentation, using in particular a peroxidase- or tyrosinase-inhibiting agent, such as gallic acid (see the claims and page 6, lines 40 to 45), for the formulation of a mask which comprises a thickening or gelling agent in the form of sodium alginate.

In addition, the document U.S. Pat. No. 6,139,829 discloses a cosmetic composition for improving the appearance of the skin and nails comprising at least one superabsorbent ionic polymer, such as a polyacrylamide/polyacrylate and/or polyacrylate compound, in particular a blend of at least one part of crosslinked sodium polyacrylate polymer and 9 parts of copolymer of acrylate and of sodium acrylate.

Finally, the document WO2004/009042 describes a mask composition comprising an emulsified liquid composition. In this context, the mask cannot be rinsed off since it necessarily comprises a conventional mask component, that is to say a solid support, for example in the form of a woven or nonwoven substrate, of a net or of a natural or synthetic sponge.

AIMS OF THE INVENTION

A main aim of the invention is to provide a novel cosmetic composition formulation of rinse-off mask type for the care of the skin, in particular of the face or body, which is simple to use and which provides an effect of freshness and of comfort during its application.

Another main aim of the invention is to provide a novel cosmetic composition formulation of rinse-off mask type for the care of the skin, in particular of the face or body, which is creamy and which provides a pleasant cosmetic feel and also an attractive visual effect.

Another main aim of the invention is to provide a novel cosmetic composition formulation of rinse-off mask type which has a good bleaching effectiveness, combined with an effect of freshness and of comfort during its application.

Another main aim of the invention is to provide a novel cosmetic composition formulation of rinse-off mask type which has a good slimming effectiveness, combined with an effect of freshness and of comfort during its application.

Another main aim of the invention is to provide a novel cosmetic composition formulation of rinse-off mask type which has a good moisturizing effectiveness, combined with an effect of freshness and of comfort during its application.

Another main aim of the invention is to provide a novel cosmetic composition formulation of rinse-off mask type which has a good calming, soothing or relaxing effectiveness, combined with an effect of freshness and of comfort during its application.

Another main aim of the invention is to provide a novel cosmetic composition formulation of rinse-off mask type having a good effectiveness in stimulating skin microcirculation for the purpose of improving the radiance of the complexion, in particular of the face, combined with an effect of freshness and of comfort during its application.

Another main aim of the invention is to provide a novel cosmetic composition formulation of rinse-off mask type having a good seboregulating effectiveness for the care of greasy skin, combined with an effect of freshness and of comfort during its application.

Another main aim of the invention is to provide a novel cosmetic composition formulation of rinse-off mask type having a good cleaning or purifying effect on the skin, combined with an effect of freshness and of comfort during its application.

Another main aim of the invention is to provide a novel cosmetic composition formulation of rinse-off mask type having a good effectiveness in combating free radicals or aging of the skin, combined with an effect of freshness and of comfort during its application.

Another main aim of the present invention is to provide such a formulation with components which make possible an easy and inexpensive cosmetic formulation which can be used on an industrial scale.

All these aims are achieved by the present invention described below.

SUMMARY OF THE INVENTION

The present invention relates to a cosmetic composition of rinse-off mask type for the care of the skin, in particular of the face or body, characterized in that it comprises at least one superabsorbent polymer or copolymer of water-retaining type, in the form of particles in the substantially completely hydrated state, said particles having, in the dry or nonhydrated state, a mean particle size of between 5 and 100 μm, advantageously of between 20 and 50 μm, in particular between 20 and 30 μm.

According to an advantageous embodiment of the invention, the mask comprises from 0.1% to 5% by weight, preferably from 0.5% to 3% by weight, with respect to the total weight of the composition, of said superabsorbent polymer or copolymer of water-retaining type.

According to another advantageous embodiment of the invention, the superabsorbent polymer or copolymer of water-retaining type is chosen from a polymer or copolymer of acrylamide, methacrylamide, N-vinylpyrrolidone, vinyl acetate, vinyl alcohol, acrylate ester or allyl alcohol type; polymer or copolymer of acrylic acid, such as polyacrylates and their salts, in particular of sodium or of potassium; polymer or copolymer of methacrylic acid and their salts; or polymers or copolymers obtained from cationic monomers of dialkylaminoalkyl acrylate or methacrylate, dialkylaminoalkylacrylamide or -methacrylamide, diallylamine or methyldiallylamine type, and their quaternary ammonium or acid salts.

These polymers or copolymers can be obtained in the presence of crosslinking agents, such as ethylene glycol diacrylate, polyethylene glycol dimethacrylate, cyanomethyl acrylate, vinyloxyethyl acrylate or methacrylate, compounds of the family of the diglycidyl ethers, and epoxy compounds, as is well known to a person skilled in the art and in particular from the document FR-2 805 461 mentioned above.

In the context of the invention, preference is given to the use, as superabsorbent polymer, of crosslinked sodium or potassium polyacrylates, such as those known commercially under the names Aqua Keep, having a mean particle size, in the dry or nonhydrated state, of between 5 and 100 μm, advantageously between 20 and 50 μm, in particular between 20 and 30 μm, in particular Aqua Keep 10 SH-NF, sold in the USA by Kobo Products Inc.

According to another advantageous embodiment of the invention, the composition is also characterized in that it comprises at least one film-forming and/or gelling/thickening agent, in particular a polysaccharide, preferably at a concentration of between 0.5% and 10% by weight, better still between 0.5% and 5% by weight, with respect to the total weight of the final composition.

This film-forming agent contributes to producing an effect of adhesion to the skin for the desired masking action. Mention may be made, as film-forming and/or gelling/thickening agent, in particular a polysaccharide, which it is possible to use in the context of the invention, of a polysaccharide obtained by fermentation, in particular a polysaccharide available commercially under the trade name Fucogel 1000 PP, sold by Solabia, France. Use may also be made of other polysaccharides, such as xanthan, hydroxyethyl cellulose, a film-forming agent with a gelling effect of synthetic type, such as acrylates/C10-30 alkyl acrylate crosspolymer or carbomer, or also a complex mixture of gelling agent available commercially and sold, for example, by Seppic, France, under the trade names Sepigel 305 and Sepiplus 400.

Use may also be made of a film-forming polymer having essentially a film-forming effect, such as a cationic polymer, in particular providing an affinity with the skin by attachment of the positive charge to the proteins of the skin, for example a copolymer of vinylpyrrolidone and of dimethylaminoethyl methacrylate quaternized with dimethyl sulfate, known under the INCI name of polyquaternium-39, such as the commercial product Merquat plus 3330 from Laboratoires Prod'Hyg, France.

According to an advantageous embodiment, the invention relates to a cosmetic composition, characterized in that it comprises, in addition to the superabsorbent polymer or copolymer and optionally the abovementioned film-forming and/or gelling/thickening polymer, at least one cosmetically active ingredient.

According to an advantageous alternative form of the invention, the cosmetically active ingredient comprises at least one cosmetically active substance chosen from the group consisting of a substance having a depigmenting activity or a lightening activity on the skin; a substance having a slimming activity; a substance having a moisturizing activity; a substance having a calming, soothing or relaxing activity; a substance having an activity in stimulating skin microcirculation in order to improve the radiance of the complexion, in particular of the face; a substance having a seboregulating activity, for the care of greasy skin; a substance intended to clean or purify the skin; a substance having an activity in combating free radicals and a substance having an antiaging activity.

Use is preferably made, as substance with a depigmenting or lightening activity on the skin, of a substance chosen from the group consisting of ascorbic acid derivatives, in particular esters, such as ascorbyl glucosides and ascorbyl phosphates, in particular magnesium ascorbyl phosphate, and an extract of fruit or of flowers of black elder (*Sambucus nigra*).

The substance having a depigmenting activity or lightening activity on the skin will advantageously be used at a concentration of between 0.001% and 5% by weight, and in particular between 0.01% and 3% by weight, with respect to the total weight of the composition.

Use may be made, as substance having a moisturizing effect, for example, of glycerol, at least one alcohol, such as an alkylene glycol and in particular propylene glycol, butylene glycol, pentylene glycol and their mixtures in all proportions, in particular those available commercially of PEG-60 type.

The composition will advantageously comprise from 0.001% to 5% by weight, preferably from 0.1% to 5% by weight, of this moisturizing agent.

Use may be made, as substance having a calming, soothing or relaxing effect, for example, of a glycyrrhizate, in particular in the form of a potassium salt. Use may be made, as substance having an activity in combating free radicals or an antiaging activity, for example, of a tocopherol acetate, preferably α-tocopherol acetate. According to a specific alternative embodiment, the proportion by weight of each of these substances will be between 0.001% and 5%.

Use may be made, as substance having a slimming effect, for example, of a xanthine, such as caffeine. According to a specific alternative embodiment, the proportion by weight of substance having a slimming effect will be between 0.001% and 5%.

Use may be made, as substance for stimulating skin microcirculation, for example, of ruscogenin. According to a specific alternative embodiment, the proportion by weight of substance for stimulating skin microcirculation will be between 0.001% and 5%.

Use may be made, as substance having a seboregulating activity for the care of greasy skin, for example, of zinc oxide or at least one zinc-based derivative, in particular organic zinc salts, such as zinc gluconate, zinc salicylate or zinc pidolate.

According to a specific alternative embodiment, the proportion by weight of substance having a seboregulating activity will be between 0.01% and 10%.

According to yet another specific embodiment of the invention, it can be advantageous to add, to said cosmetic composition, at least one refreshing agent, such as, for example, menthol or a derivative of the latter, such as menthoxypropanediol.

According to another embodiment of the invention, the cosmetic composition can be formulated in the form of a mask which can be applied to a region of the skin in need of cosmetic care, for example of the face, or to the thighs or hips.

In the context of the cosmetic composition of the present invention, in the form of a rinse-off mask, the use of the superabsorbent polymer or copolymer in the form of essentially completely hydrated particles provides the surprising effect of the structuring of the cosmetic formulation while making it easy to rinse off this mask, which provides the advantage of reducing the amounts of other excipient(s) supplied, as is easily understandable by a person skilled in the art. In the context of the invention, use may be made of any cosmetically acceptable excipient in the manufacture of such a composition.

Such excipients suitable for the manufacture of a cosmetic composition, in particular in the form of a mask, comprise one or more preservatives and also other ingredients commonly used in cosmetics, such as plasticizers, fillers of a coloring material, such as pigments, waxes, surfactants, oils; a solubilizer, such as, for example, castor oil, in particular in the hydrogenated form, with polyethylene glycol; or fragrances, which are well known to a person skilled in the art.

A person skilled in the art knows in addition to choose excipients or the other active ingredients, and their concentration, so that the advantageous properties of the composition of the invention are well retained.

According to a second aspect, the present invention also covers the use of the superabsorbent polymer or copolymer in the manufacture of a cosmetic composition of rinse-off mask type for the care of a region of the skin, in particular of the face or body, comprising said superabsorbent polymer or copolymer as defined above or as defined in the following description, optionally in combination with at least one film-forming agent and/or gelling/thickening agent, in particular a polysaccharide, and preferably with at least one other cosmetically active ingredient as defined in the present description or with a cosmetically acceptable excipient as defined in the present description.

According to a third aspect, the present invention also covers a cosmetic care method, characterized in that it comprises the application, to the skin of a person desiring cosmetic care, of a composition as defined in the present description for a period of time sufficient to obtain the desired cosmetic effect.

According to an advantageous embodiment of the invention, this cosmetic care method is targeted at producing a cosmetic effect chosen from the group consisting of a depigmenting effect or lightening effect on the skin; of a moisturizing effect on the skin; of a calming, soothing or relaxing effect; of an effect in combating free radicals on the skin; of an antiaging effect on the skin; of a slimming effect; of an effect for stimulating skin microcirculation for the purpose of improving the radiance of the complexion, in particular of the face; of a purifying or cleaning effect on the skin; and of a seboregulating effect for the care of greasy skin.

Other aims, characteristics and advantages of the invention will become clearly apparent in the light of the explanatory description which will follow, made with reference to two exemplary embodiments of a mask according to the invention given solely by way of illustration and which should therefore in no way limit the scope of the invention.

In the examples, all the percentages are given by weight, with respect to the total weight of the composition; the temperature is ambient temperature; the pressure is atmospheric pressure, unless otherwise indicated.

EXAMPLE 1 ACCORDING TO THE INVENTION

Cosmetic Composition in the Form of a Mask Having a Bleaching Effect and an Effect in Combating Free Radicals A mask having a bleaching effect is prepared from the following percentage composition:
a) superabsorbent polymer based on crosslinked sodium polyacrylate, in the form of substantially completely hydrated particles, available commercially under the trade name Aqua Keep 10 SH-NF, having a mean particle size in the dry or nonhydrated state of between 20 and 30 μm, Kobo Products Inc: 1.6%
b) at least one cosmetically active ingredient comprising:
  i) at least one substance having a depigmenting or lightening activity on the skin, for example:
    magnesium ascorbyl phosphate: approximately 0.01%
    extract of fruit and/or of flowers of elder (Sambucus nigra): 0.1%
  ii) at least one substance having an activity in combating free radicals or an antiaging activity, for example α-tocopherol acetate: 0.001%
c) cosmetically acceptable excipient comprising:
preservative (benzyl benzoate, paraben, in particular in the form of a mixture of ethyl-, propyl-, butyl- and isobutylparaben): approximately 0.001% in total,
water-dispersible pearlescent agent, such as mica black: approximately 1%
d) purified water: q.s. for 100%

The mask of the invention is prepared from the above composition in the following way:
a) in a first stage, an aqueous phase is prepared by successively mixing, in water, all the components other than the superabsorbent polymer; and
b) in the final mixing stage, the superabsorbent polymer is added and the mixture is left standing until absorption of the water by the superabsorbent polymer is complete, the mask thus being obtained.
After application to the skin of the face for 10 min, the mask is rinsed off with water, advantageously warm water for the comfort of the user.

EXAMPLE 2 ACCORDING TO THE INVENTION

Cosmetic Composition in the Form of a Bleaching and Moisturizing Mask

This mask is prepared from the following percentage composition:
a) superabsorbent polymer or copolymer based on crosslinked sodium polyacrylate available commercially under the trade name Aqua Keep 10 SH-NF, having a mean particle size in the dry or nonhydrated state of between 20 and 30 μm, Kobo Products Inc., in the form of substantially completely hydrated particles: 1.6% b) at least one cosmetically active ingredient comprising:
   i) at least one substance having a depigmenting or lightening activity on the skin, for example:
      ascorbic acid 2-glucoside: approximately 2%
      extract of fruit and/or of flowers of elder (*Sambucus nigra*): 0.1%
   ii) at least one moisturizing substance, for example glycerol: 3%
c) film-forming and/or gelling or thickening agent, in particular a polysaccharide, especially Fucogel 1000 PP: 3%
d) water, fragrances, preservatives: remainder to 100%

First of all an aqueous phase is prepared comprising the water to which the various ingredients, other than the superabsorbent polymer and the gelling or thickening agent, are added.

In a second stage, first of all the gelling or thickening agent and subsequently the superabsorbent agent are added with stirring in order to obtain a substantially homogeneous mixture. The mixture is left standing in order to bring about the complete absorption of the water.

The ready-for-use mask is thus obtained.

The superabsorbent agent used in the context of the invention to manufacture the mask provides a very refreshing effect by contributing water and visually a noteworthy effect of the product in itself of frost type. In the case of example 1, a black pigment was used; the black frost effect for a product having a bleaching effect is very attractive to the clientele.

After application to the skin of the face for 10 min, the mask is rinsed off with water, advantageously warm water for the comfort of the user.

What is claimed is:

1. A cosmetic rinse-off mask composition for the care of the skin, comprising
   from 0.5 to 5 weight percent, with respect to the total weight of the composition, of at least one water-retaining superabsorbent polymer that is a crosslinked sodium or potassium polyacrylate in the form of particles in a substantially completely hydrated state, said particles having, in the dry or nonhydrated state, a mean particle size of between 20 and 30 μm;
   at least one agent that is a film forming agent, a gelling agent, or a thickening agent, the at least one agent comprising a polysaccharide and being at a concentration of between 0.5 and 10 weight percent, with respect to the total weight of the composition; and
   a substance having a moisturizing effect at a concentration of between 0.1% and 5% by weight, with respect to the total weight of the composition.

2. The composition of claim 1 further comprising at least one other cosmetically active ingredient.

3. The composition of claim 2, wherein the at least one other cosmetically active ingredient comprises at least one cosmetically active substance, wherein the substance has a depigmenting or lightening activity on the skin, a slimming activity, a calming, soothing or relaxing activity, an activity in stimulating skin microcirculation for the purpose of improving the radiance of the complexion, in particular of the face, or a seboregulating activity, for the care of greasy skin, or an activity in combating free radicals and a substance having an antiaging activity, or is intended to clean or purify the skin.

4. The composition of claim 1, further comprising a substance having a depigmenting or lightening activity on the skin, wherein the substance is an ascorbic acid ester, an ascorbyl glucoside, ascorbyl phosphate, magnesium ascorbyl phosphate, or an extract of fruit or flowers of black elder (*Sambucus nigra*).

5. The composition of claim 1, further comprising a substance having a depigmenting activity or lightening activity on the skin at a concentration ranging between 0.001% and 5% by weight, with respect to the total weight of the composition.

6. The composition of claim 1, wherein the substance having a moisturizing effect is glycerol.

7. The composition of claim 1, further comprising a substance having a calming or soothing or relaxing effect, at a concentration ranging between 0.001% and 5% by weight, with respect to the total weight of the composition.

8. The composition of claim 7, wherein the substance having a calming, soothing or relaxing effect is a glycyrrhizate or a glycyrrhizate potassium salt.

9. The composition of claim 1, further comprising a substance having a slimming effect at a concentration ranging between 0.001% and 5% by weight, with respect to the total weight of the composition.

10. The composition of claim 9, wherein the substance having a slimming effect is a xanthine.

11. The composition of claim 1, further comprising a substance for stimulating skin microcirculation at a concentration ranging between 0.001% and 5% by weight, with respect to the total weight of said composition.

12. The composition of claim 11, wherein the substance for stimulating skin microcirculation is ruscogenin.

13. The composition of claim 1, further comprising a substance having a seboregulating activity for the care of the skin, at a concentration ranging between 0.01% and 10% by weight, with respect to the total weight of said composition.

14. The composition of claim 1, further comprising a substance having a seboregulating activity for the care of the skin, wherein the substance is zinc oxide, an organic zinc salt, zinc gluconate, zinc salicylate, or zinc pidolate.

15. The composition of claim 1, further comprising a substance having an activity for combating free radicals, at a concentration ranging between 0.001% and 5% by weight, with respect to the total weight of said composition.

16. The composition of claim 15, wherein the substance having an activity for combating free radicals is a tocopherol ester, or an α-tocopherol ester.

17. The composition of claim 1, further comprising at least one refreshing agent.

18. The composition of claim 17, wherein the at least one refreshing agent is menthol or menthoxypropanediol.

19. The composition of claim 1, formulated in the form of a mask to be applied to a region of the skin in need of cosmetic care.

20. A method of cosmetic care comprising applying to a region of the skin of a person in need of cosmetic care a cosmetically effective amount of a composition as defined in claim 1.

21. The method of claim 20, wherein the cosmetic care is a depigmenting or lightening care on the skin, a moisturizing care on the skin, a calming skin care, a soothing skin care, a relaxing skin care, a slimming care, a care for stimulating skin microcirculation, a care for stimulating skin microcirculation of the skin face, a care of greasy skin, a cleaning skin care, a purifying skin care, a care for combating free radicals, or an antiaging skin care.

22. A cosmetic rinse-off mask composition for the care of the skin comprising:
   at least one water-retaining superabsorbent polymer that is a crosslinked sodium or potassium polyacrylate in the form of particles in a substantially completely hydrated state, said particles having, in the dry or nonhydrated state, a mean particle size of between 20 and 30 μm;

at least one agent that is a film-forming agent, a gelling agent or a thickening agent that comprises a polysaccharide that is xanthan or hydroxyethylcellulose, the polysaccharide being at a concentration of between 0.5 and 10 by weight percent, with respect to the total weight of the composition; and a substance having a moisturizing effect at a concentration of between 0.1% and 5% by weight, with respect to the total weight of the composition.

23. A cosmetic rinse-off mask composition for the care of the skin comprising about 1.6 weight percent, with respect to the total weight of the final composition, of a crosslinked sodium polyacrylate having a mean particle size of between 20 and 30 µm;

at least one agent that is a film forming agent, a gelling agent, or a thickening agent, the at least one agent comprising a polysaccharide and being at a concentration of about 3 weight percent, with respect to the total weight of the composition; and a substance having a moisturizing effect at a concentration of between 0.1% and 5% by weight, with respect to the total weight of the composition.

24. The composition of claim 1, wherein the polysaccharide is xanthan or hydroxyethylcellulose.

25. The composition of claim 23, wherein the polysaccharide is xanthan or hydroxyethylcellulose.

* * * * *

UNITED STATES PATENT AND TRADEMARK OFFICE
CERTIFICATE OF CORRECTION

PATENT NO. : 8,394,363 B2
APPLICATION NO. : 12/281736
DATED : March 12, 2013
INVENTOR(S) : Claire Jonchiere It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this

First Day of September, 2015

Michelle K. Lee
*Director of the United States Patent and Trademark Office*